United States Patent
Anderson

(12) 
(10) Patent No.: US 6,403,317 B1
(45) Date of Patent: Jun. 11, 2002

(54) ELECTRONIC DETECTION OF HYBRIDIZATION ON NUCLEIC ACID ARRAYS

(75) Inventor: Rolfe C. Anderson, Saratoga, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/535,142

(22) Filed: Mar. 24, 2000

Related U.S. Application Data

(60) Provisional application No. 60/126,461, filed on Mar. 26, 1999.

(51) Int. Cl.[7] .................. C12Q 1/68; C12M 1/36; G01N 15/06; G01N 31/12
(52) U.S. Cl. .................. 435/6; 435/287.2; 435/288.7; 422/68.1; 422/82.01; 422/82.05; 422/82.12
(58) Field of Search .................. 435/6, 288.7, 287.2; 422/68.1, 82.01, 82.05, 82.12

(56) References Cited

U.S. PATENT DOCUMENTS

| | | | |
|---|---|---|---|
| 4,490,216 A | 12/1984 | McConnell | |
| 4,591,550 A | 5/1986 | Hafeman et al. | |
| 4,704,353 A | 11/1987 | Humphries et al. | |
| 4,758,786 A | 7/1988 | Hafeman | |
| 4,849,330 A | 7/1989 | Humphries et al. | |
| 4,883,579 A | 11/1989 | Humphries et al. | |
| 4,911,794 A | 3/1990 | Parce et al. | |
| 4,963,815 A | 10/1990 | Hafeman | |
| 5,164,319 A | 11/1992 | Hafeman et al. | |
| 5,605,662 A | * 2/1997 | Heller et al. | 422/68.1 |
| 5,653,939 A | * 8/1997 | Hollis et al. | 422/50 |
| 5,824,481 A | * 10/1998 | Kambara et al. | 435/6 |
| 5,849,486 A | 12/1998 | Heller et al. | 435/6 |
| 6,068,818 A | 5/2000 | Ackley et al. | 422/50 |
| 6,093,370 A | * 7/2000 | Yasuda et al. | 422/68.1 |
| 6,099,803 A | 8/2000 | Ackley et al. | 422/68.1 |
| 6,159,686 A | * 12/2000 | Kardos et al. | 435/6 |

FOREIGN PATENT DOCUMENTS

| | | |
|---|---|---|
| EP | 0510725 | 10/1992 |
| WO | WO 85/04018 | 9/1985 |
| WO | WO 90/04645 | 5/1990 |
| WO | WO 94/03791 | 2/1994 |

OTHER PUBLICATIONS

Taton et al., "Scanometric DNA array detection with nanoparticle probes" Science (2000) 289:1757–1760.

* cited by examiner

Primary Examiner—W. Gary Jones
Assistant Examiner—BJ Forman
(74) Attorney, Agent, or Firm—Philip L. McGarrigle; Alan B. Sherr; Ivan D. Zitkovsky

(57) ABSTRACT

A method of detecting locations on a nucleic acid probe array at which hybridization occurs between targets in a fluid sample and nucleic acid probes disposed on a surface of the nucleic acid probe array, comprising: measuring the temperature at a plurality of locations on the surface of the nucleic acid probe array; applying an oscillating level of energy to the surface of the nucleic acid probe array, thereby causing the temperature at the surface of the nucleic acid probe array to oscillate; and detecting a decreased range of temperature oscillation at least one of the plurality of locations on the nucleic acid probe array, thereby indicating an increased heat capacity caused by latent heat of hybridization between at least one target in the fluid sample and at least one nucleic acid probe disposed on a surface of the nucleic acid probe array.

16 Claims, 6 Drawing Sheets

ELECTRONIC DETECTION OF HYBRIDIZATION ON NUCLEIC ACID ARRAYS

CROSS-REFERENCES TO RELATED APPLICATIONS

The present application is a regular patent application of and claims the benefit of priority from U.S. patent application Ser. No. 60/126,461 filed Mar. 26, 1999 the full disclosure of which is incorporated herein by reference.

TECHNICAL FIELD

The present invention relates to systems for detecting hybridization between targets in a fluid sample and nucleic acid probes disposed on the surface of a nucleic acid probe array.

BACKGROUND OF THE INVENTION

Nucleic acid probe arrays are used for detecting the presence of various target molecules in a fluid sample. The nucleic acid probes are preferably fabricated directly onto the surface of the probe array using light directed synthesis. As the fluid sample is passed over the surface of the probe array, the target molecules will hybridize with corresponding nucleic acid sequences which are attached to the surface of the probe array.

The target molecules are preferably prepared with tags, such as fluorescin, in order to discriminate areas of strong hybridization to the probes on the array. Specifically, a laser is directed at various discreet locations on the probe array, and fluorescent light is emitted at hybridization locations. By knowing the location of various nucleic acid probe sequences attached to the array (i.e.: when the array was initially fabricated), and by determining the locations at which hybridization has occurred (by detecting fluorescence emissions therefrom), it is then possible to determine whether various target molecules are present in the fluid sample.

Typically, a microscopic scanning system is used to detect the locations of hybridization between the target molecules in fluid sample and the probes on the surface of the probe array. Unfortunately, a disadvantage of optical scanning of the probe array to determine hybridization locations is that it requires a complex scanning and fluorescence detection optical system. As such, precise optics are required which are adapted to discriminate between various microscopically small locations on the surface of the probe array. Moreover, a further disadvantage of detecting hybridization by an optical system is that observation of the behavior of each probe over a range of conditions is often difficult.

SUMMARY OF THE INVENTION

The present invention provides systems for detecting locations of hybridization on the surface of a nucleic acid probe array between targets present in a fluid sample and nucleic acid probes disposed on the surface of the probe array.

In a preferred aspect, the present invention comprises measuring the temperature at a plurality of discreet locations on the surface of the probe array while applying an oscillating level of energy to the probe array, thereby causing the temperature of the probe array to oscillate.

By detecting a decreased range of temperature oscillation at least one of a plurality of locations on the probe array, hybridization is detected at the at least one of a plurality of locations on the probe array. Specifically, a decreased range of temperature oscillation at the particular location on the probe array (in response to a steady oscillation of energy applied to the array) is indicative of an increase in heat capacity at that location due to the latent heat of hybridization between at least one target in the fluid sample, and at least one nucleic acid probe disposed at the particular location in question on the surface of the probe array.

At the point of hybridization between the probe and the target molecules, the apparent heat capacity at the probe/target interface will increase. This increased heat capacity can be sensed as a decreased oscillating thermal response. Accordingly, by detecting a spike in the apparent heat capacity at the nucleic acid probe/substrate interface (the surface of the probe array), hybridization can be detected.

In various preferred aspects of the invention, the oscillating level energy applied to the surface of the probe array is applied by a heater disposed under the probe array. Preferably, an array of heaters is disposed under the probe array with each heater being disposed under a small "patch" of probes.

An advantage of the present invention is that the need for optical scanning of the probe array to detect hybridization location is overcome. Consequently, the need to preparer the target molecules with a tag such as fluorescin is also overcome.

Hybridization bond energies between probes which are attached to the probe array and target molecules in the fluid sample may vary widely, thus resulting in widely variant equilibrium constants which may experience some hysteresis as the stringency (temperature or ionic trough) is varied.

Accordingly, an optional advantage of using an array of heaters with each heater being disposed under a patch of probes is that it is possible to adjust the temperature under each patch of probes to a temperature which is approximately equal to the temperature at which hybridization occurs between probes at a particular patch of probes and targets in the fluid sample. An advantage of adjusting the temperature at each patch of probes (by each heater) is that the probe site can be optimized for detecting hybridization. This translates to a higher quality signal, at a larger probe range. As such, a further advantage of the present system is that it may provide a better signal for determining true vs. near matches.

In preferred aspects of the invention, a temperature monitoring system is used to measure the temperature at the plurality of locations on the nucleic acid probe array. This temperature monitoring system may preferably comprise a differential scanning calorimetry system. In alternate aspects of the present invention, an infrared scanner may be used to measure the temperature at a plurality of locations on the surface of the probe array.

In an exemplary aspect of the invention, the heaters are formed on suspended diaphragms of silicon nitrate and the heaters are made of polycrystalline silicon.

In an alternate embodiment, the nucleic acid probe array is disposed over an optically absorbing material (for example, a thin nickel film) which is in turn disposed over a thermal insulation layer. In an exemplary aspect of the invention, this thermal insulation layer comprises a material selected from the group consisting of a ceramic, silicon or glass.

In this alternate embodiment of the present invention, the application of an oscillating level of energy to the surface of the probe array is performed by directing the outputs of first and second lasers at the surface of the probe array. In this embodiment of invention, the first laser is preferably adapted to control the "gross" or a large scale temperature at the probe array with a second laser being adapted to "fine tune" the oscillating temperature at the probe array. As such, the second laser acts as a "probe" laser, and an infrared scanner is preferably used to detect the transient heating signal from the probe (ie: second) laser.

In yet another embodiment of the present invention, an electrode is positioned in the target liquid, an insulating layer is positioned under the nucleic acid probe array and a silicon n-p-n junction is disposed underneath the insulating layer.

In this alternate embodiment of the invention, a laser beam is directed at the under side of the n-p-n junction, thereby forming a circuit between the n-p-n junction and the electrode in the target liquid. By measuring the impedance of this circuit, hybridization can be detected. In preferred aspects of this invention, the laser beam is scanned back and forth across the underside of the n-p-n junction, thereby measuring the impedance of the resulting circuit at a plurality of discrete locations on the nucleic acid probe array.

An advantage of this embodiment of the present invention is that the laser beam unblocks small localized regions of the n-p-n junction, thus avoiding the problem of parasitic capacitance. As such, hybridization can be detected at small discreet locations on the probe array without interference from hybridization at adjacent locations on the on the probe array. By avoiding the problem of parasitic capacitance, a high spatial resolution can be achieved. Specifically, parasitic capacitance is decreased in the present system by the creation of a lightly doped blocking diode region under the nucleic acid probe array and an optical beam (such as a laser beam) is then be used to unblock this region.

The silicon layer is protected from the target liquid by the insulating layer. In an exemplary aspect, the insulating layer comprises silicon nitride, silicon carbide, diamond-like carbon, or boron nitride.

A depletion region will form in the silicon layer adjacent to the insulating layer. The n-p-n junction forms an additional depletion region which reduces the parasitic capacitance.

Moreover, the AC impedance of the circuit will be sensitive to changes close to the insulating layer within a distance defined as the Debye layer. By scanning the laser light beam across the underside of the system, a local hybridization pattern can be determined.

In accordance with this embodiment of the present invention, hybridization locations may be detected electronically by: 1) detecting a shift in double-layer capacitance resulting from a change in the dielectric constant, 2) detecting a shift in the point of zero charge in a semiconductor electrolyte interface, and 3) detecting a shift in the zeta potential of the insulating layer. The second and third mechanisms preferably require a semiconductor substrate.

In various alternate embodiments, the p-n junction is eliminated; photocurrent is used to measure surface changes, an ion sensitive material is placed over the insulating layer; and/or the device may be defined on an insulator using SOI technology to reduce parasitic capacitance.

BRIEF DESCRIPTION OF THE DRAWINGS

Lastly.

DESCRIPTION OF THE SPECIFIC EMBODIMENTS

Figure 1:
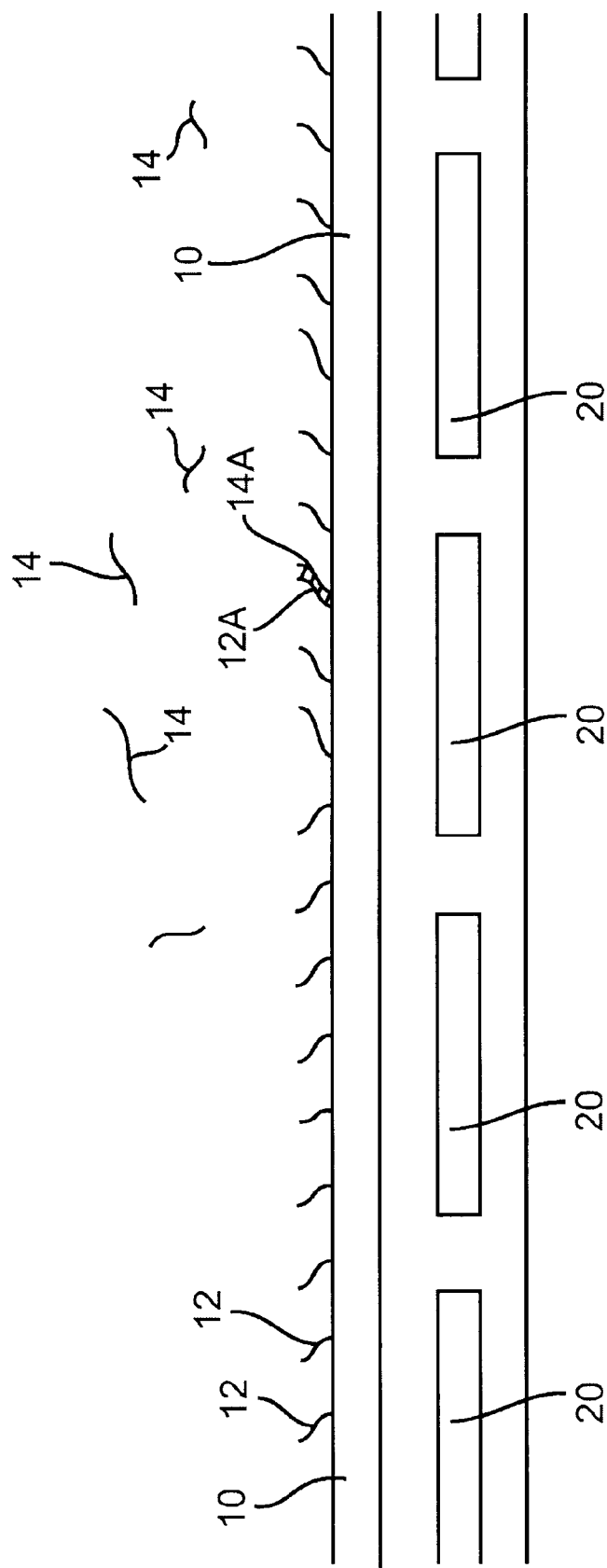
FIG. 1 is a sectional elevation view of a first embodiment of the present invention.

Referring first to FIG. 1, a first embodiment of the present invention is provided. A nucleic acid probe array 10 is provided having a plurality of nucleic acid sequences (ie: probes) 12 attached thereto. A plurality of target molecules 14 (freely floating within a fluid sample) are passed over the surface of array 10. When a target molecule (14A) corresponds identically to an opposite probe sequence (12A) hybridization will occur, as shown.

The present invention provides systems for detecting hybridization (for example between probe 12A and target molecule 14A) by detecting the location on array 10 at which such hybridization has occurred. Since the identity and location of probe 12A is known when array 10 is initially fabricated, the presence of target molecule 14A in the fluid sample can be confirmed simply by detecting hybridization at the location occupied by probe 12A on array 10.

In a first embodiment of the present invention, a plurality of heaters 20 are disposed underneath the probes 12 on array 10, as shown.

In accordance with the present invention, the temperature is measured at various discreet locations on the probe array while an oscillating (or otherwise varying) level of energy is applied to the probe array, for example by heating heaters 20.

In one aspect of the invention, the temperature of probe array 10 is oscillated and hybridization is detected by sensing a decrease in the range of temperature oscillation at the location of hybridization, (which is caused by an increased heat capacity caused by the latent heat of hybridization between the probe and the target molecule).

In an alternate approach, the energy applied to probe array 10 is varied (e.g.: increased), with continuous temperature monitoring showing a decrease or "dip" in the rate of increase of the temperature at that location when hybridization occurs. Conversely, the temperature of probe array 10 may be decreased, (by allowing the array to cool) with a decrease or "dip" in the rate of decrease of the temperature at a location on the probe array also indicating that hybridization has occurred.

Figure 2:
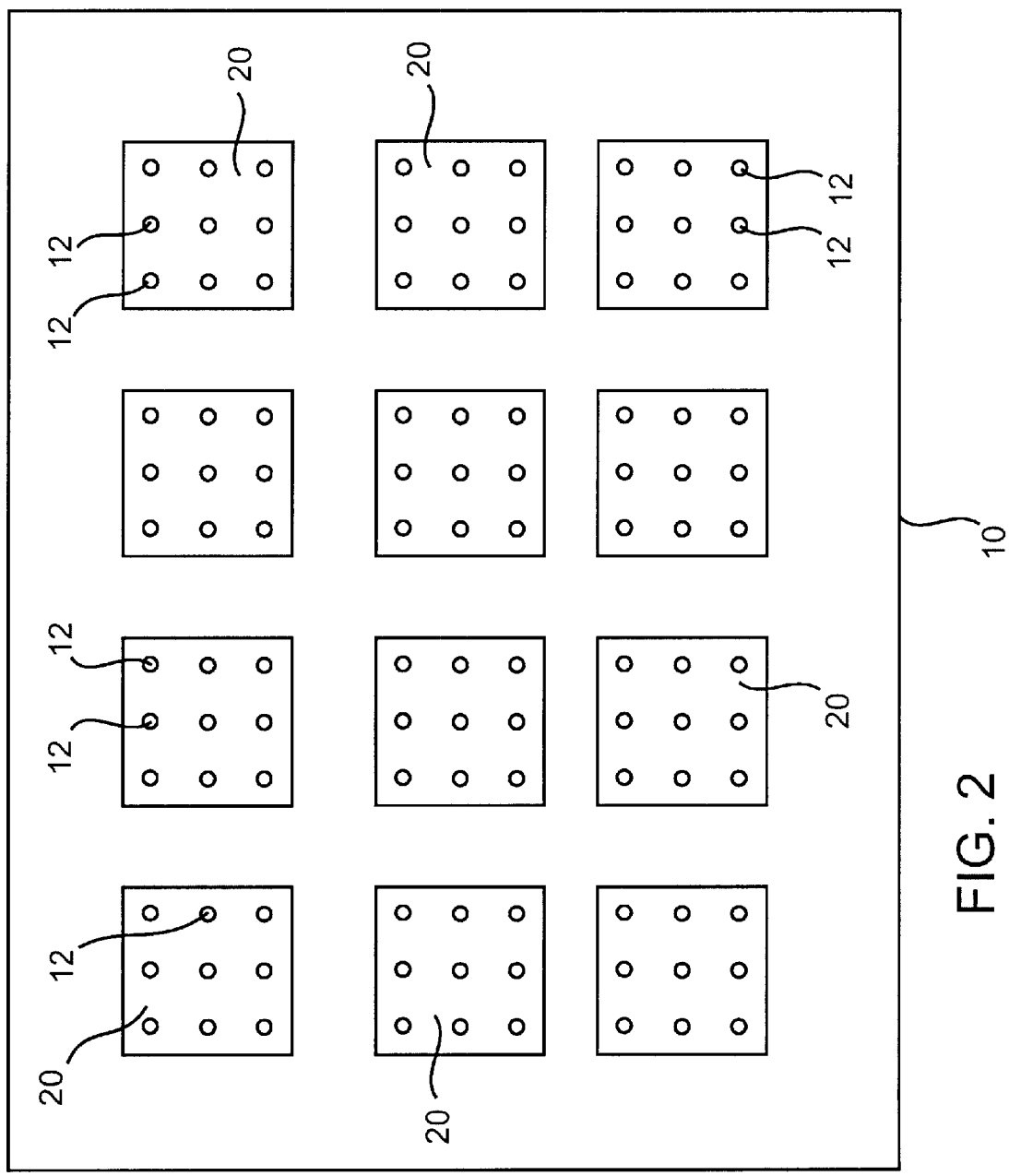
FIG. 2 is a top schematic view of an array of heaters disposed under "patches" of nucleic acid probes on a nucleic acid probe array.

As show in FIG. 1, each of heaters 20 may be disposed under a "patch" of probes. In a preferred aspect, heaters 20 are each produced to be very small such that each resides under a minimum number of probes 12. As such, it is possible to operate each of heaters 20 such that the temperature of the probe(s) disposed over the heater can be as close as possible to the temperature at which hybridization actually occurs between a particular probe(s) and it's corresponding target sequence(s). Having a plurality of heaters 20 disposed in an array under patches of probes (see FIG. 2) allows different portions of array 10 to be adjusted to different temperatures, thereby enhancing signal results.

Figure 3:
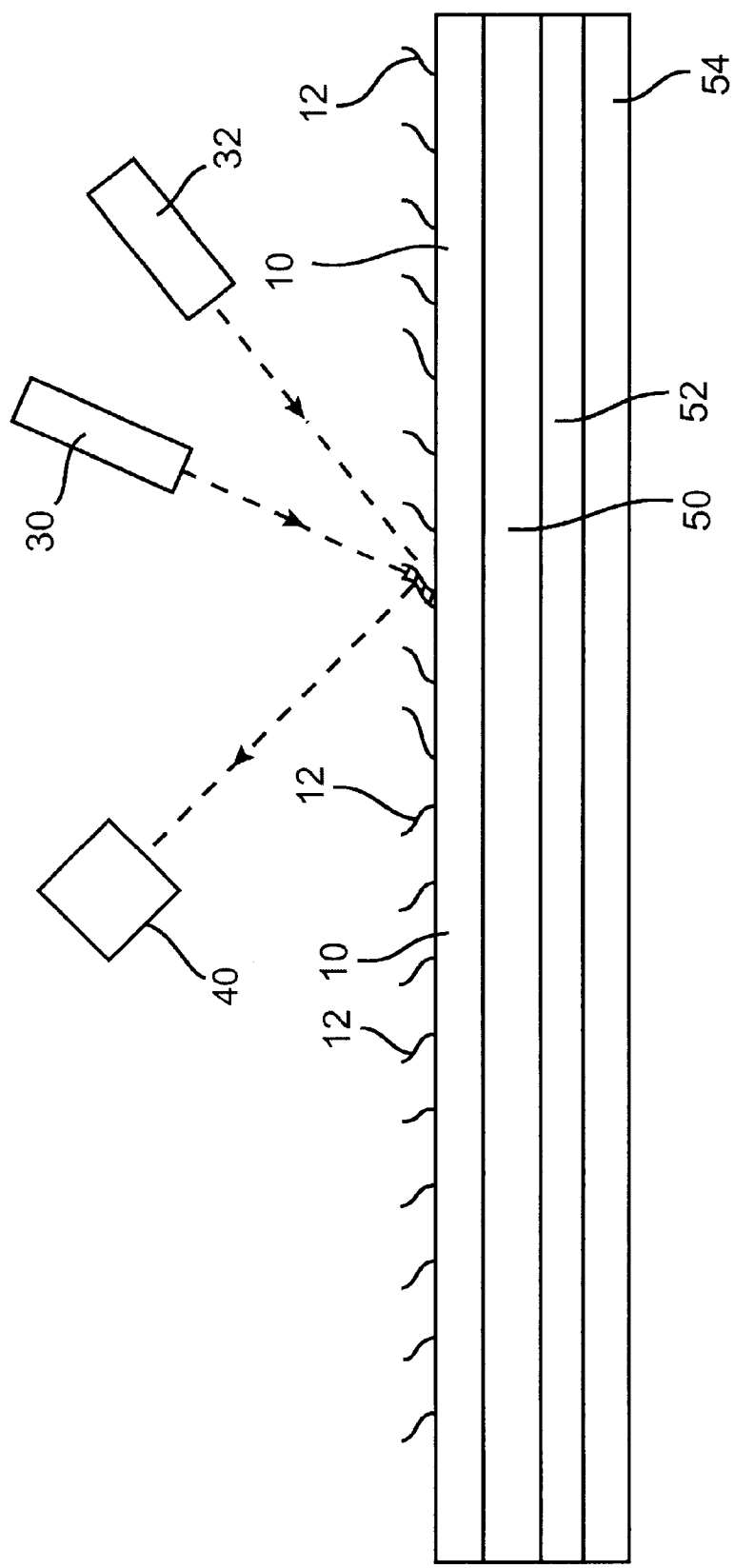
FIG. 3 is a sectional elevation view of a second embodiment of the present invention.

FIG. 3 shows a second embodiment of the present invention in which energy is applied to the surface of probe array 10 by a first laser 30 and a second laser 32. In an exemplary aspect, first laser 30 controls the "gross" temperature at the surface of array 10 and second laser 32 is operated to "fine tune" the temperature at the surface of array 10. An infrared scanner 40 may be used to measure the temperature at each of the plurality of discreet locations on array 10, with the temperature response measured at each of these locations being used to determine whether hybridization has occurred, using any of the methods as explained above.

In this second embodiment, a light absorbing layer 50, a thermal insulation layer 52 and a ceramic, silicon or glass substrate 54 may be positioned under array 10 as shown.

Figure 4:
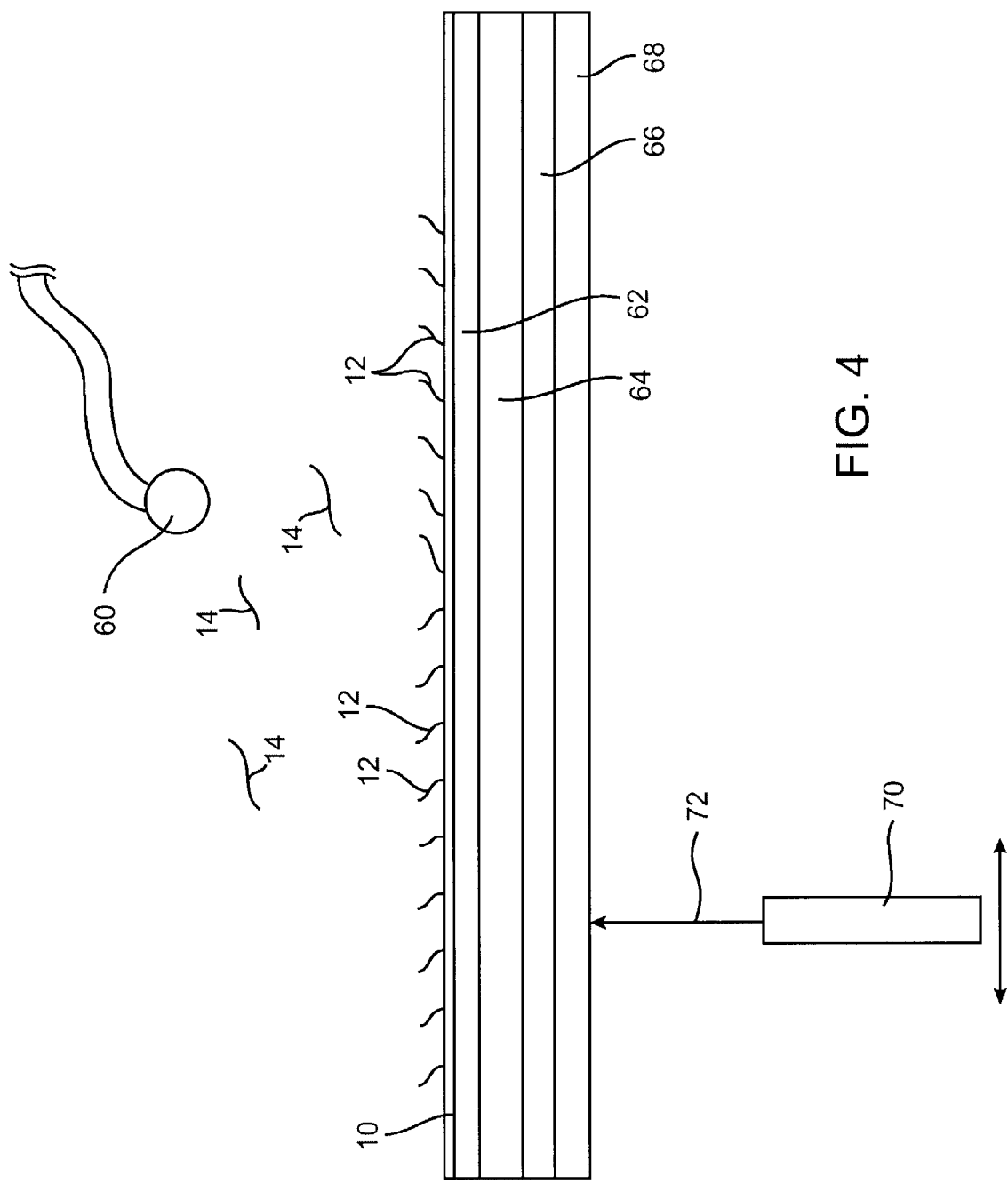
FIG. 4 is a sectional elevation view of a third embodiment of the present invention.

In a third embodiment of the present invention, as shown in FIG. 4, an electrode 60 is positioned in the target liquid which is passed over the surface of array 10. An insulating layer 62 is disposed under array 10 and an n-p-n junction (formed from n-type doped silicon layer 64, p-type doped silicon layer 66, and n-type doped silicon layer 68) is disposed under insulating layer 62, as shown.

A laser 70 scans a laser beam 72 across the underside of the n-p-n junction, forming a circuit between the n-p-n junction and electrode 60. By measuring the impedance of this circuit (with only the location at which laser beam 72 strikes the underside of the n-pn junction being unblocked), the pattern of hybridization can be detected across array 10.

Figure 5:
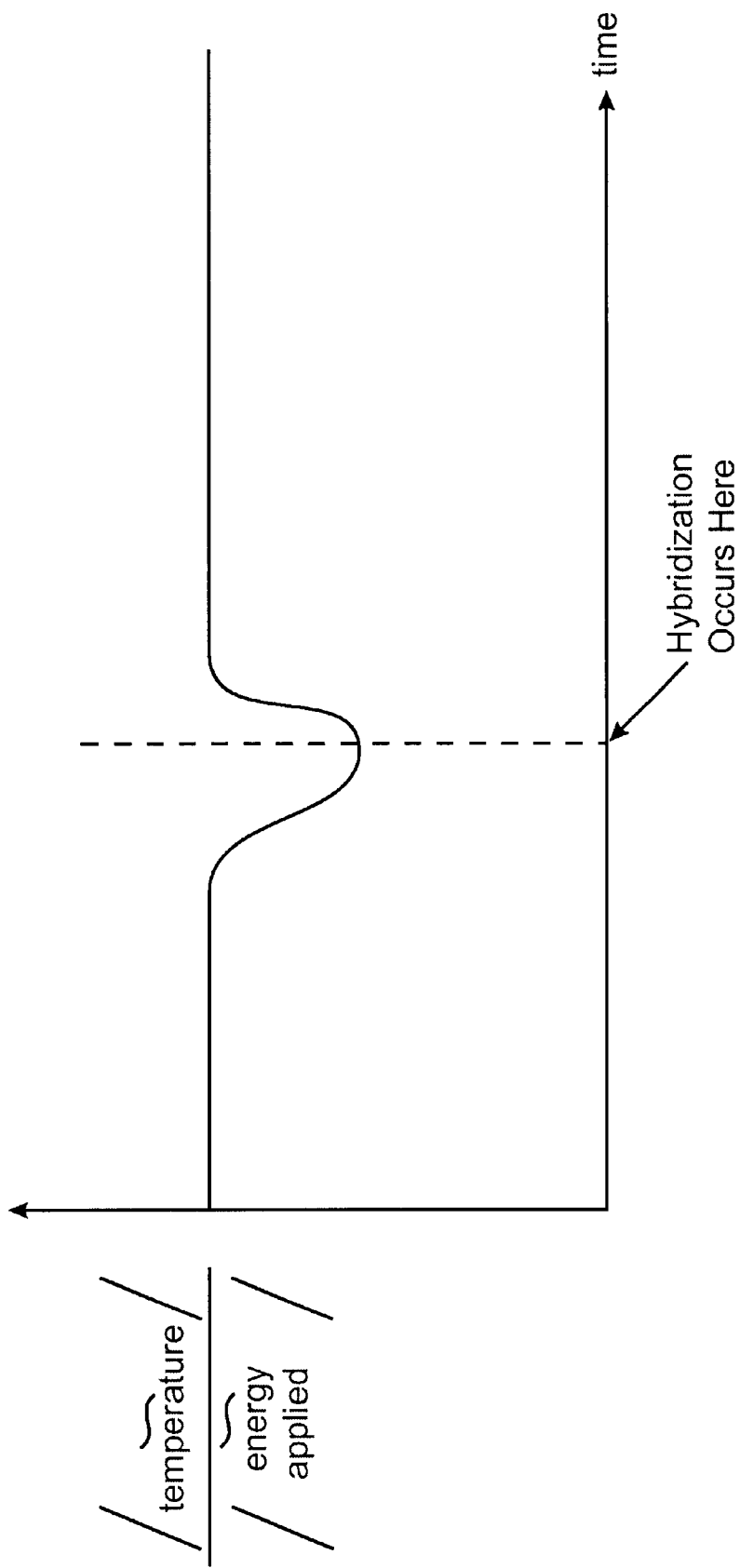
FIG. 5 is a graph showing the relationship over time between the measured temperature and the energy applied to a location on the probe array at which hybridization occurs.

FIG. 5 illustrates the relationship over time between the measured temperature and the energy applied to a location on the probe array at which hybridization occurs, with the point at which hybridization occurs being shown as a decrease in the temperature relative to the amount of energy applied to the surface of the probe array.

Figure 6:
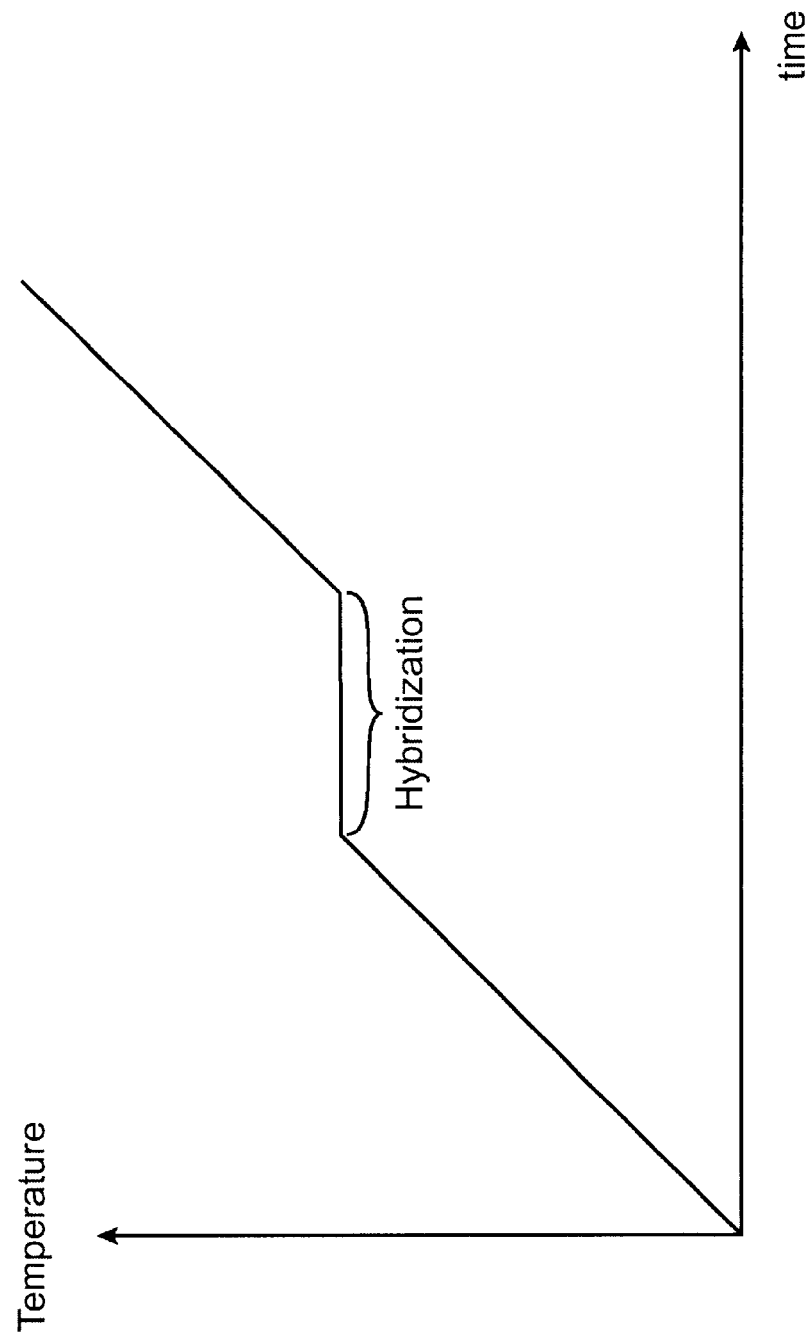
FIG. 6 shows the relationship between time and temperature at a location on the probe array at which hybridization has taken place, in the case where the energy applied to the probe array is continuously increased over time.

Lastly, FIG. 6 shows the relationship over time of the temperature of the probe array at a location on the probe array at which hybridization has taken place, in the case where the energy applied to the probe array is continuously increased over time

What is claimed is:

1. A method of detecting locations on a nucleic acid probe array at which hybridization occurs between targets in a fluid sample and nucleic acid probes attached to a surface of the nucleic acid probe array, comprising:
   measuring the temperature at a plurality of locations on the surface of the nucleic acid probe array;
   applying energy to the surface of the nucleic acid probe array, thereby causing the temperature at the surface of the nucleic acid probe array to increase; and
   detecting a decrease in the rate of temperature change at least one of the plurality of locations, where hybridization has occurred, compared to the rate of temperature change at another of the plurality of locations, where hybridization has not occurred, on the nucleic acid probe array, said decrease being due to an increased heat capacity caused by hybridization between at least one target in the fluid sample and at least one nucleic acid probe disposed on a surface of the nucleic acid probe array at said at least one hybridization location.

2. A method of detecting locations on a nucleic acid probe array at which hybridization occurs between targets in a fluid sample and nucleic acid probes attached to a surface of the nucleic acid probe array, comprising:
   measuring the temperature at a plurality of locations on the surface of the nucleic acid probe array;
   decreasing the temperature of the surface of the nucleic acid probe array; and
   detecting a decrease in the rate of temperature change at least one of the plurality of locations, where hybridization has occurred compared to the rate of temperature change at another of the plurality of locations, where hybridization has not occurred, on the nucleic acid probe array, said decrease being due to an increased heat capacity caused by hybridization between at least one target in the fluid sample and at least one nucleic acid probe disposed on a surface of the nucleic acid probe array at said at least one hybridization location.

3. The method of claim 1 or 2 including an array of heaters, each heater being disposed under a patch of probes.

4. The method of claim 3, further comprising:
   adjusting the temperature at each patch of probes to a temperature approximately equal to the temperature at which hybridization occurs between the patch of probes and the targets.

5. The method of claim 1 or 2 further comprising:
   providing an optically absorbing layer under the probe array;
   providing a thermal insulation layer under the optically absorbing material; and
   providing a substrate under the thermal insulation layer.

6. The method of claim 5, wherein the substrate comprises a material selected from the group consisting of a ceramic, silicon or glass.

7. The method of claim 5, wherein the optically absorbing layer comprises a thin nickel film.

8. The method of claim 1 or 2, wherein said measuring includes using an infrared scanner to measure the temperature at a plurality of locations on the surface of the nucleic acid probe array.

9. The method of claim 1, wherein applying energy to the surface of the nucleic acid probe array is accomplished by at least one heater disposed under the nucleic acid probe array.

10. The method of claim 9, wherein the at least one heater comprises an array of heaters, each heater being disposed under a patch of probes.

11. The method of claim 10, further comprising:
   adjusting the temperature at each patch of probes to a temperature approximately equal to the temperature at which hybridization occurs between the patch of probes and the targets.

12. A method of detecting locations on a nucleic acid probe array at which hybridization occurs between targets in a fluid sample and nucleic acid Probes attached to a surface of the nucleic acid probe array, comprising:
   measuring the temperature at a plurality of locations on the surface of the nucleic acid probe array;
   applying an oscillating amount of energy to the surface of the nucleic acid probe array including directing the output of a first laser at the surface of the nucleic acid probe array and directing the output of a second laser at the surface of the nucleic acid probe array, wherein the output of the first laser is greater than the output of the second laser, thereby causing the temperature at the surface of the nucleic acid probe array to oscillate; and
   detecting a decreased range of temperature oscillation at least one of the plurality of locations, where hybridization has occurred, compared to a range of temperature oscillation at another of the plurality of locations, where hybridization has not occurred, on the nucleic acid probe array, said decreased range being due to an increased heat capacity caused by hybridization between at least one target in the fluid sample and at least one nucleic acid probe disposed on a surface of the nucleic acid probe array at said at least one hybridization location.

13. The method of claim 12, wherein the first laser is adapted to control the average temperature at the probe array, and the second laser is adapted to fine tune the temperature at the probe array.

14. The method of claim 1, 2 or 12, wherein said measuring includes detecting a shift in double-layer capacitance resulting from a change in a dielectric constant.

15. The method of claim 1, 2 or 12, wherein said measuring includes detecting a shift in a point of zero charge in a semiconductor electrolyte interface.

16. The method of claim 1, 2 or 12, wherein said measuring includes detecting a shift in the zeta potential of an insulating layer.

* * * * *